US012133926B2

(12) United States Patent
Childress et al.

(10) Patent No.: US 12,133,926 B2
(45) Date of Patent: Nov. 5, 2024

(54) SANITIZING SYSTEM

(71) Applicant: THE BOEING COMPANY, Chicago, IL (US)

(72) Inventors: Jamie J. Childress, Mercer Island, WA (US); Colin Diehl, Chicago, IL (US); Mateus Daczko, Chicago, IL (US); Nels Olson, Chicago, IL (US)

(73) Assignee: The Boeing Company, Chicago, IL (US)

( * ) Notice: Subject to any disclaimer, the term of this patent is extended or adjusted under 35 U.S.C. 154(b) by 726 days.

(21) Appl. No.: 17/352,724

(22) Filed: Jun. 21, 2021

(65) Prior Publication Data

US 2021/0393823 A1     Dec. 23, 2021

Related U.S. Application Data

(60) Provisional application No. 63/042,898, filed on Jun. 23, 2020.

(51) Int. Cl.
 *A61L 2/10*     (2006.01)

(52) U.S. Cl.
 CPC ............. *A61L 2/10* (2013.01); *A61L 2202/11* (2013.01); *A61L 2202/14* (2013.01); *A61L 2202/25* (2013.01)

(58) Field of Classification Search
 CPC ................................ A61L 2/10; A61L 2202/25
 See application file for complete search history.

(56) References Cited

U.S. PATENT DOCUMENTS

| | | | |
|---|---|---|---|
| 2009/0108649 A1* | 4/2009 | Kneller | ........... B64D 11/00 244/129.1 |
| 2014/0179212 A1 | 6/2014 | Space | |
| 2016/0089459 A1 | 3/2016 | Boodaghians | |
| 2017/0080117 A1 | 3/2017 | Gordon | |
| 2017/0246331 A1* | 8/2017 | Lloyd | ........... A61Q 17/04 |
| 2018/0209613 A1 | 7/2018 | Callahan | |
| 2019/0030195 A1* | 1/2019 | Hatti | ........... A61L 2/24 |
| 2020/0073199 A1* | 3/2020 | Lin | ........... A61L 2/0047 |

FOREIGN PATENT DOCUMENTS

| | | | | |
|---|---|---|---|---|
| CA | 3121354 A1 * | 10/2019 | ........... | A61L 2/10 |
| CN | 111 110 890 | 5/2020 | | |
| DE | 202020001197 U1 * | 5/2020 | ........... | A61L 2/10 |
| JP | 2018 007804 | 1/2018 | | |
| WO | WO 2019/068189 | 4/2019 | | |

OTHER PUBLICATIONS

DE-202020001197-U1 Translation (Year: 2020).*
Extended European Search Report for EP 21181076.7-1010, dated Nov. 9, 2021.
Welch David et al: "Far-UVC Light: A New Tool to Control the Spread of Airborne Mediated Microbial Diseases", Scientific Reports, vol. 8, No. 2752 (Dec. 1, 2018), pp. 1-7.

* cited by examiner

*Primary Examiner* — Kevin Joyner
*Assistant Examiner* — Changru Chen
(74) *Attorney, Agent, or Firm* — Joseph M. Butscher; The Small Patent Law Group, LLC

(57) ABSTRACT

A sanitizing system includes a plurality of ultraviolet (UV) lamps mounted at various locations within an internal cabin of a vehicle. The UV lamps are configured to receive electrical power from a power source onboard the vehicle and to emit UV light into the internal cabin on a continuous basis during a trip of the vehicle. The UV lamps are positioned such that the emitted UV light disinfects air within the internal cabin.

21 Claims, 4 Drawing Sheets

SANITIZING SYSTEM

CROSS-REFERENCE TO RELATED APPLICATIONS

This application relates to and claims priority benefits from U.S. Provisional Patent Application No. 63/042,898, filed Jun. 23, 2020 and entitled "Sanitizing System," which is hereby incorporated by reference in its entirety.

FIELD OF THE DISCLOSURE

Embodiments of the present disclosure generally relate to systems and methods that may be used to sanitize structures and air within enclosed areas, such as vehicle cabins.

BACKGROUND OF THE DISCLOSURE

Vehicles such as commercial aircraft are used to transport passengers between various locations. Systems are currently being developed to disinfect or otherwise sanitize surfaces to kill or neutralize various harmful microbes or other pathogens. Typical methods of sanitizing surfaces within aircraft involve significant manual effort by one or more crew members. For example, some crew members may spray and wipe cleaning chemicals on surfaces within an internal cabin of the aircraft. Other crew members may slowly wave a wand that emits ultraviolet (UV) radiation on nearby surfaces of the internal cabin. The UV radiation can kill or neutralize some microbes or other pathogens if held at a certain proximity to a target surface for at least a designated amount of time.

Furthermore, many commercial vehicles such as aircraft have HEPA filters in the air conditioning system that are able to entrap microbes and pathogens. The HEPA filters receive and clean air exiting the cabin or about to enter the cabin. HEPA filters and frequent cleaning of the cabin between flights are some methods to ensure the health of the passengers and crew onboard the aircraft. Additional sanitizing methods could be used to supplement the HEPA filters and chemical cleanings.

SUMMARY OF THE DISCLOSURE

A need exists for a system and a method for prohibiting the spread of pathogens between passengers onboard a vehicle during a trip, such as between passengers in an internal cabin of an aircraft during a flight, without risking harm to the passengers.

With those needs in mind, certain embodiments of the present disclosure provide a sanitizing system that includes a plurality of ultraviolet (UV) lamps mounted at various locations within an internal cabin of a vehicle. The internal cabin includes seats. The UV lamps are configured to receive electrical power from a power source onboard the vehicle and to emit UV light into the internal cabin on a continuous basis during a trip of the vehicle. The UV lamps are positioned such that the emitted UV light disinfects air within the internal cabin.

In one or more embodiments, a method for sanitizing a vehicle is provided. The method includes supplying electrical power from a power source onboard a vehicle to a plurality of ultraviolet (UV) lamps mounted at various locations within an internal cabin of the vehicle. The method also includes controlling the UV lamps to emit UV light into the internal cabin on a continuous basis during a trip of the vehicle. The UV lamps are positioned such that the emitted UV light disinfects air within the internal cabin before passengers in the internal cabin breathe the air.

In one or more embodiments, a sanitizing system is provided that includes a plurality of ultraviolet (UV) lamps mounted at various locations within an internal cabin of a vehicle. The UV lamps are configured to receive electrical power from a power source onboard the vehicle. The sanitizing system also includes a control unit operatively connected to the UV lamps. The control unit is configured to control the UV lamps to emit UV light into the internal cabin on a continuous basis during a trip of the vehicle. The control unit is configured to modify the electrical power supplied to one or more of the UV lamps during the trip based on activity of the passengers such that the one or more UV lamps receive more electrical power when the passengers are more active than when the passengers are less active.

DETAILED DESCRIPTION OF THE DISCLOSURE

Figure 1:
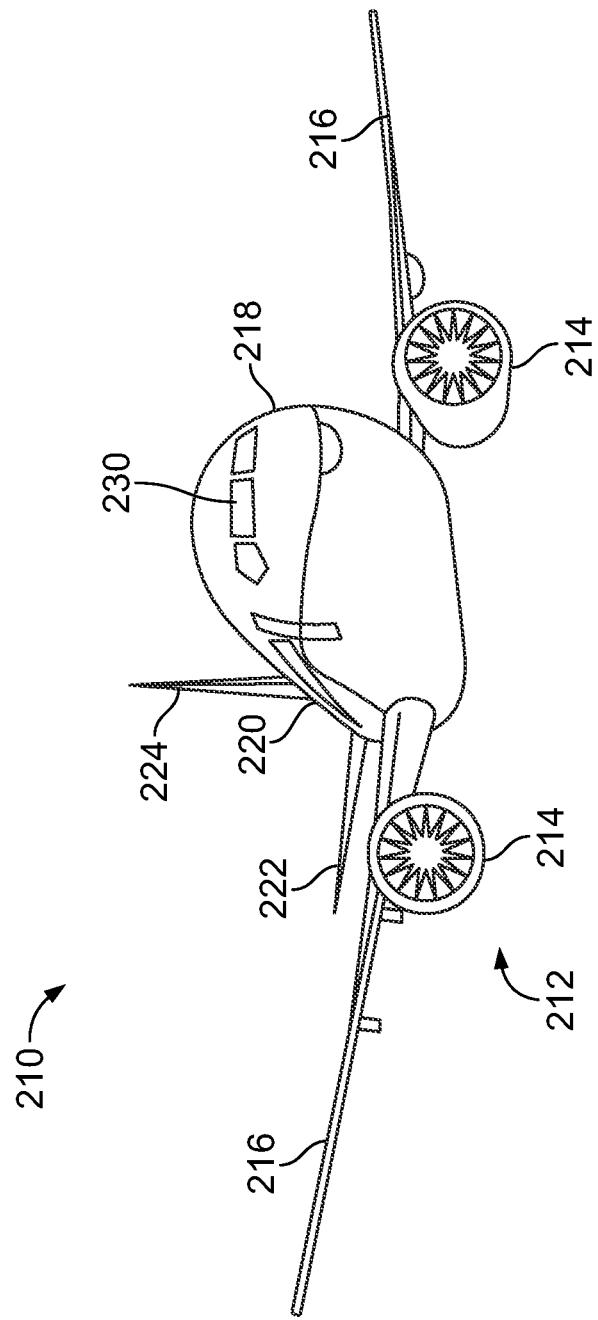
FIG. 1 illustrates a perspective front view of an aircraft, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system and method for disinfecting the internal cabin of a vehicle, such as a commercial aircraft. The sanitizing system includes a group of ultraviolet (UV) lamps arranged within the internal cabin. The UV lamps are positioned and controlled to emit UV light into the internal cabin during travel of the vehicle such that the UV light sanitizes air and surfaces within the internal cabin. The UV lamps may be controlled to emit filtered UV light at a designated wavelength or narrow wavelength range that is safe for human tissue. For example, the designated wavelength may be 222 nm. The UV lamps are positioned to sanitize air in breathing areas in and around passenger heads to kill or neutralize pathogens that may be directly spread between occupants, such as between two passengers or between a passenger and a crew member. For this purpose, at least some of the UV lamps may be located above the passenger seats, such as adjacent to personal visible-wavelength lights and personal blower vents (or puffers) that emit conditioned air towards one or more passengers in a row. Additional UV lamps may be disposed along the ceiling above aisles, within galleys, within lavatories, and the like, to emit UV light in areas trafficked by onboard occupants (e.g., passengers and crew).

In at least one embodiment, the UV lamps are operated to persistently emit UV light for extended periods of time. For example, the UV lamps may be ON to emit UV light throughout an entire duration of a trip, from the time that passengers board the vehicle to the time that passengers deboard. The persistent UV emission serves to kill or neutralize pathogens to prohibit the spread of pathogens in the air and on surfaces during travel of the vehicle, between cabin cleanings. For example, the UV light may kill pathogens in the air between two conversing occupants in the cabin. The HEPA filters in the environmental control system (e.g. air conditioning system) would not be able to prevent the direct spread of pathogens between two conversing occupants because the HEPA filters only treat air after the air is pulled from the cabin.

In at least one embodiment, even though persistently operated, the sanitizing system may modulate or vary the output of the UV lamps based on passenger activity and/or occupancy. Activity refers to the physical movement and interactions of passengers. Occupancy refers to the number of passengers and location of passengers in the cabin. For example, the sanitizing system may be configurable in different modes or settings based on measured or expected activity of the passengers. The activity can be based on trip status, such as whether the passengers are boarding or seated in place with seatbelts on. The activity can also be based on time of day, as activity is expected to be greater during the day than at night when most people are reading, watching videos, and sleeping. The different settings may cause the UV lamps to emit UV light at different power levels. A higher power level increases the intensity and/or range of the emitted UV light, relative to a lower power level. The greater intensity and/or range could kill or neutralize a greater amount or percentage of pathogens in the field of illumination per unit time, but the higher power level also draws more electrical power than lower power levels (so is less efficient). In an embodiment, the sanitizing system can control the UV lamps at the different settings to sanitize the cabin while conserving energy. In a non-limiting example related to occupancy, the sanitizing system could be configured to turn off or at least reduce the power provided to UV lamps located in areas devoid of passengers relative to UV lamps located proximate to passengers, which can conserve energy and increase energy efficiency.

One or more technical effects of the sanitizing system include reducing the spread of pathogens between occupants (e.g., passengers and crew members) of a vehicle during a trip of the vehicle. For example, the sanitizing system particularly prohibits the direct spread of pathogens through the air before the air can be filtered by the onboard environmental control system. The sanitizing system also can sanitize surfaces to prevent the spread of pathogens via touch before the cabin can be cleaned between trips. Another technical effect is that the presence and operation of the sanitizing system does not negatively impact the passengers or the enjoyment of the trip, as the persistent filtered UV light emitted by the sanitizing system is not distracting and does not harm the passengers. Furthermore, although operating the UV lamps requires energy and a power supply, the sanitizing system can modulate the settings of the UV lamps based on activity and occupancy to reduce the energy consumed (relative to perpetually operating at a medium or high power setting), which desirably limits power consumption without sacrificing passenger health and safety. The sanitizing system may ensure compliance with regulations that require a safe environment within the cabin of the aircraft during a flight.

FIG. 1 illustrates a perspective front view of an aircraft 10, according to an embodiment of the present disclosure. The aircraft 10 includes a propulsion system 12 that includes engines 14, for example. Optionally, the propulsion system 12 may include more engines 14 than shown. The engines 14 are carried by wings 16 of the aircraft 10. In other embodiments, the engines 14 may be carried by a fuselage 18 and/or an empennage 20. The empennage 20 may also support horizontal stabilizers 22 and a vertical stabilizer 24.

The fuselage 18 of the aircraft 10 defines an internal cabin, which includes a flight deck or cockpit, one or more work sections (for example, galleys, personnel carry-on baggage areas, and the like), one or more passenger sections (for example, first class, business class, and coach sections), one or more lavatories, and/or the like.

Alternatively, instead of an aircraft, embodiments of the present disclosure may be used with various other vehicles, such as automobiles, buses, rail vehicles, watercraft, and the like. For example, the sanitizing system disclosed herein can be implemented in an internal cabin of a passenger train, a bus, a passenger boat, and the like. Embodiments of the present disclosure may be used with respect to enclosed areas within fixed structures, such as commercial and residential buildings. For example, the sanitizing system and method disclosed herein can be installed and operated within theatres, concert venues, places of worship, office buildings, stores, and the like, where persistent UV light at non-harmful wavelengths can provide continuous disinfection of air and surfaces.

Figure 2:
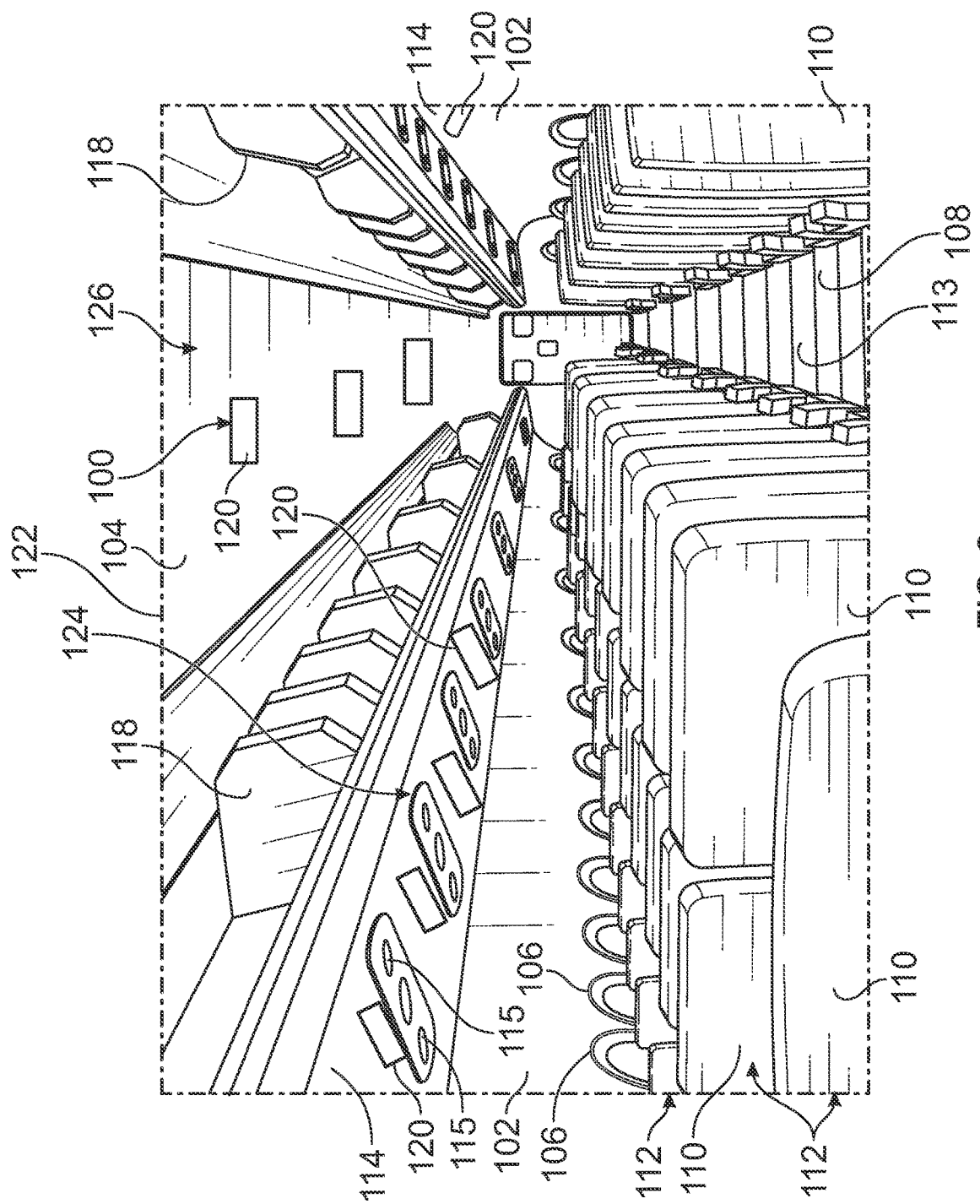
FIG. 2 illustrates a perspective view of a sanitizing system within a portion of an internal cabin of the aircraft according to an embodiment of the present disclosure.

FIG. 2 illustrates a perspective view of a sanitizing system 100 within a portion of an internal cabin 122 of the aircraft 10 according to an embodiment of the present disclosure. The internal cabin 122 includes outboard walls 102 connected to a ceiling 104. Windows 106 may be formed within the outboard walls 102. A floor 108 supports rows of seats 110. A row 112 may include three seats 110 on either side of an aisle 113. However, the row 112 may include more or less seats 110 than shown. Additionally, the internal cabin 122 may include more than the single aisle 113 shown in FIG. 2.

Passenger service units (PSUs) 114 are secured between the outboard wall 302 and the ceiling 104 on either side of the aisle 113. The PSUs 114 are arranged in longitudinal columns that extend between a front end and rear end of the internal cabin 122. For example, at least one PSU 114 may be positioned over the seats 110 within a row 112 on either side of the aisle 113. The PSUs 114 may include personal air blowers 115 (e.g., or vents, puffers, etc.), reading lights, oxygen bag drop panels, attendant request buttons, and other such controls and components. At least some of the controls and components of the PSU 114 may be shared between groups of two or three seats 110 in the row 112, such as the reading light. Other components may be specific to individual seats 110, such as the personal air blowers 115.

Overhead stowage bin assemblies 118 are secured to the ceiling 104 and/or the outboard wall 102 above the PSU 114 on either side of the aisle 113. The overhead stowage bin assemblies 118 are secured over the seats 110. The overhead stowage bin assemblies 118 are configured to be pivoted open in order to receive passenger carry-on baggage and personal items, for example. As used herein, the term "outboard" means a position that is further away from a central longitudinal plane of the internal cabin 122 as compared to another component, and the term "inboard" means a position that is closer to the central longitudinal plane of the internal cabin 122 as compared to another component.

The sanitizing system 100 includes a plurality of ultraviolet (UV) lamps 120 mounted within the internal cabin 122. The UV lamps 120 are controlled to generate and emit UV light into the internal cabin 122 to sanitize and disinfect air and surfaces within the internal cabin 122. The UV lamps 120 may be located at various areas throughout the internal cabin 122. In the illustrated embodiment, a first subset 124 of UV lamps 120 are mounted to the PSUs 114 above the passenger seats 110. For example, the UV lamps 120 in the PSUs 114 may be disposed proximate to other components of the PSUs 114 such as the air blowers 115 and the reading lights. In an embodiment, the UV lamps 120 in the first subset 124 are integrated into the PSUs 114 such that each UV lamp 120 emits UV light into an associated row 112 of seats 110 on one side of the aisle 113. Depending on the field of illumination or spread at which the UV light is emitted from each UV lamp 120, each PSU 114 may include only one or multiple UV lamps 120. The field of illumination refers to refers to a three-dimensional volume in space that is defined by the propagation of UV light waves (e.g., rays) emitted by the UV lamp 120. The width of the field of illumination can depend on mechanical features of the UV lamp 120, such as reflectors, collimators, lenses, and the like, and optionally may be set to provide a predetermined width. In a non-limiting embodiment, the field of illumination of the UV lamps 120 in the PSUs 114 may be sufficient for each UV lamp 120 to sanitize the air and surfaces around two passenger seats 110. Thus, for groups of three or more seats 110 in a row 112 on one side of the aisle 113, the PSU 114 may include at least two UV lamps 120 with one UV lamp 120 located outboard of another UV lamp 120 to enable the combined UV light to cover the entire group of seats 110 and the passengers seated thereon. In another non-limiting embodiment, the number of UV lamps 120 in the first subset 124 may match the total number of seats 110 such that each UV lamp 120 is specifically directed to and associated with a different seat 110 in the internal cabin 122.

A second subset 126 of UV lamps 120 of the sanitizing system 100 is mounted to the ceiling 104 between the overhead stowage bin assemblies 118. The UV lamps 120 in the second subset 126 are aligned in a linear column that extends a length of the internal cabin 122 between the front and rear ends. The UV lamps 120 in the second subset 126 are spaced apart along the length. The spacing between the UV lamps 120 may be based on the field of illumination or spread of the UV light emitted from the UV lamps 120 to ensure that there is at least some overlap in the coverage areas of two adjacent UV lamps 120 at a designated height above the floor 108 to avoid creating dead zones that could harbor pathogens. The subset 126 may emit UV light that shines all the way down to the floor 108 within the aisle 113. The UV light from the subset 126 may essentially form a sanitization wall that partitions the internal cabin 122.

Although two subsets 124, 126 or groupings of UV lamps 120 are shown in FIG. 2, the UV lamps 120 may be located in other areas of the cabin 122 as well, such as in galleys, in lavatories, at partitions between sections, and the like. In general, the UV lamps 120 of the sanitizing system 100 are positioned throughout the cabin 122 to maximize the coverage area of the UV light. Maximizing the coverage area refers to emitting UV light to cover a substantial amount or percentage of the area or volume within the cabin 122, such as over 80%, over 90%, over 95%, or the like, particularly in areas occupied and trafficked by passengers and crew. The UV light sanitizes and disinfects the air and surrounding surfaces. The surrounding surfaces that can be disinfected by the UV light can include the seats 110 (including arm and headrests thereof), tray tables, personal computers used by the passengers, skin and clothing of the passengers and crew, walls of the cabin 122, doors, and the like. The sanitizing system 100 is configured to persistently operate the UV lamps 120 in the on, emitting state even in the presence of passengers, such as during boarding, taxiing, flight, and deboarding. Unlike current practices which only provide intermittent disinfection, such as chemically cleaning the cabin 122 between flights and filtering a given volume of air every time that volume of air is pulled through a return register of an environmental control system, the sanitizing system 100 disinfects pathogens on surfaces and in the air on a continuous basis.

Figure 3:
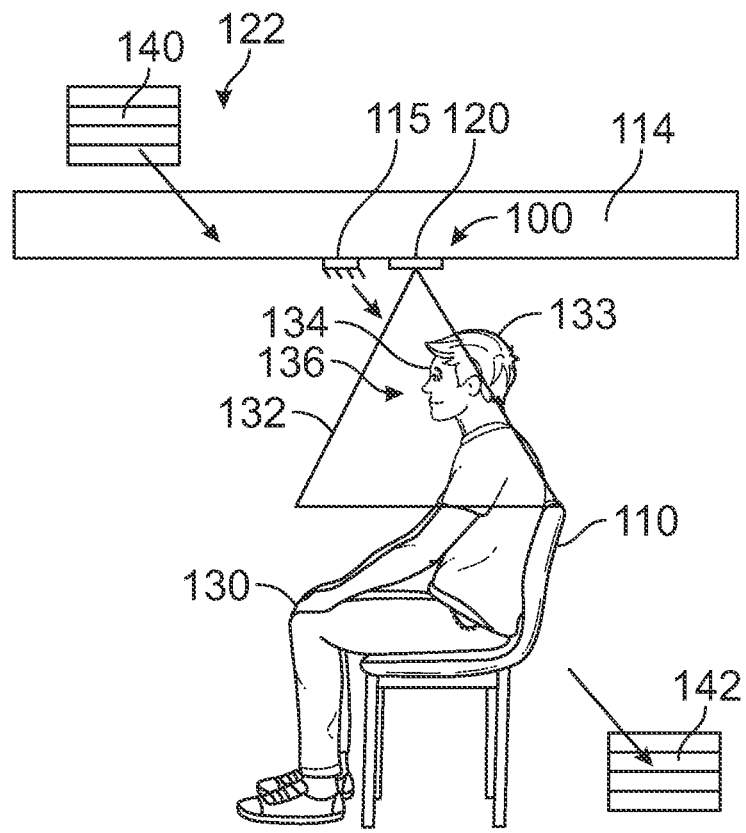
FIG. 3 illustrates one UV lamp of the sanitizing system according to an embodiment.

FIG. 3 illustrates one of the UV lamps 120 of the sanitizing system 100 according to an embodiment. The UV lamp 120 that is illustrated is in the PSU 114 above a seat 110 that is occupied by a passenger 130. In one or more embodiments, the UV lamp 120 is located and oriented to sanitize contaminated air before that air touches and/or is inhaled by the passenger 130. For example, the UV lamp 120 has a field of illumination 132 that encompasses the passenger's head 133, or at least face 134, when the passenger 130 is sitting in the seat 110 facing forward. As such, air that is breathed by the passenger 130 travels through the UV light and is sanitized. Stated differently, the UV lamp 120 is positioned to emit UV light into a breathing area 136 in front of the passenger's face 134, which protects the passenger 130 from airborne pathogens, such as during conversations with other passengers and crew members.

The illustrated embodiment shows that the UV light is emitted into a flow path of air through the cabin 122. For example, air from an environmental control system or air conditioning system is supplied into the cabin 122 via a supply vent 140 and a personal air blower (or vent) 115. The supply vent 140 may be disposed along a wall or ceiling of the cabin 122, such as above the stowage bin assemblies 118 shown in FIG. 2. The personal air blower 115 is a component of the PSU 114, and may have a manually adjustable damper to selectively regulate the direction and/or flow rate of air. A return register 142 or vent is configured to collect air from the cabin 122 and cycle the air back through the environmental control system. The return air may be filtered through at least one HEPA filter. As shown in FIG. 3, the supply vent 140 and blower 115 are disposed above the seat 110, and the return register 142 is disposed below the seat 110, such as at or near the floor. The air through the cabin 122 generally flows downward from the supply vent 140 and the blower 115 to the return register 142. The UV lamp 120 directs UV light into the air flow path at a location between the passenger 130 and the supply vent 140 and/or blower 115.

In an embodiment, the UV lamp is controlled and/or the UV light is filtered to enable the passenger 130 to be exposed to the UV light for a prolonged period of time without harm to the passenger 130. For example, the emitted UV light may have a designated wavelength or a narrow band of wavelengths experimentally determined to be harmless to human tissue through prolonged exposure. Thus, even if the UV lamp 120 persistently emits UV light through the duration of the flight, the passenger 130 is unharmed. The UV lamp 120 may be configured or constructed to only generate the designated wavelength or the narrow band.

Alternatively, a filter may be utilized that absorbs or dissipates wavelengths outside of the designated wavelength or the narrow band such that emitted UV light in the field of illumination 132 shown in FIG. 3 only consists of the designated wavelength or the narrow band.

In a non-limiting example, the designated wavelength is 222 nm. It has been found that sanitizing UV light having a wavelength of 222 nm kills pathogens (such as viruses and bacteria), instead of inactivating pathogens. In contrast, UVC light at a wavelength of 254 nm inactivates pathogens by interfering with their DNA, resulting in temporary inactivation, but may not kill the pathogens. Instead, the pathogen may be reactivated by exposure to ordinary white light at a reactivation rate of about 10% per hour. As such, UVC light at a wavelength of 254 nm may be ineffective in illuminated areas, such as within an internal cabin of a vehicle. Moreover, UVC light at 254 nm is not recommended for human exposure because it may be able to penetrate human cells. In contrast, sanitizing UV light having a wavelength of 222 nm is safe for human exposure and kills pathogens. Further, the sanitizing UV light having a wavelength of 222 nm may be emitted at full power within one millisecond or less of the UV lamps 120 being activated (in contrast the UVC light having a wavelength of 254 nm, which may take seconds or even minutes to reach full power).

Figure 4:
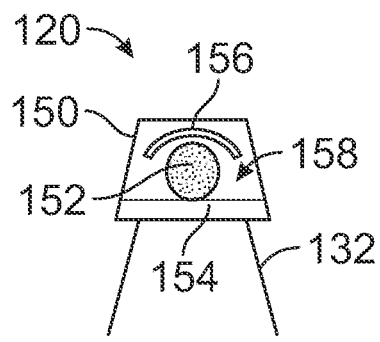
FIG. 4 illustrates a side view of one UV lamp of the sanitizing system according to an embodiment.

FIG. 4 illustrates a side view of one of the UV lamps 120 of the sanitizing system 100 according to an embodiment. The UV lamp 120 includes a housing 150, a bulb 152, a cover sheet 154 or lens, and a reflector 156. The bulb 152 and the reflector 156 are held within a cavity 158 defined by the housing 150 and the cover sheet 154. The bulb 152 emits UV light that penetrates through the cover sheet 154, which is transparent or at least translucent, into the field of illumination 132. The reflector 156 is reflective and arranged such that the bulb 152 is between the reflector 156 and the cover sheet 154. The reflector 156 is shaped and positioned to reflect light that impinges on the surface of the reflector 156 towards the cover sheet 154. The reflector 156 may be curved at least partially around the bulb 152. The walls of the housing 150 may be opaque, and optionally reflective, to prevent light transmission through the walls, ensuring that the field of illumination 132 is defined by light transmitted through the cover sheet 154. The UV lamp 120 may include additional components, such as a convex lens or a concave lens, hardware for mounting the bulb 152 to the housing 150, and circuitry for supplying electrical power to the bulb 152.

In an embodiment, the field of illumination 132 is static and consistent during operation of the UV lamp 120. For example, the reflector 156 may be mounted in a fixed position within the housing 150. In an alternative embodiment, the reflector 156 may be able to rotate or swivel to change the dimensions of the field of illumination 132.

Figure 5:
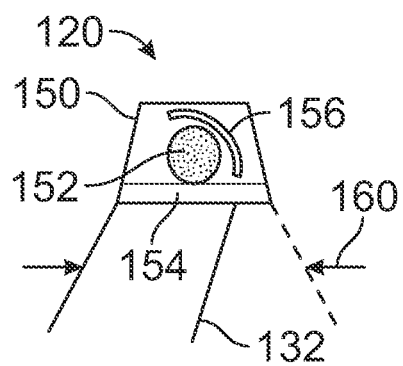
FIG. 5 illustrates a side view of the UV lamp of the sanitizing system according to another embodiment.

FIG. 5 illustrates a side view of one of the UV lamps 120 of the sanitizing system 100 according to another embodiment. The reflector 156 is coupled to an actuator that is controlled to swivel and/or translate the reflector 156 to change the angle of the reflector 156 relative to the bulb 152 and the cover sheet 154. In the illustrated position, the reflector 156 is off-center to the right and the field of illumination 132 (shown in solid lines) is skewed to the left. As the reflector 156 is gradually moved to a position off-center to the left, the field of illumination 132 (not shown) shifts to the right. As a result, over multiple cycles, the UV light is transmitted into a wider illumination area 160 than the static lamp 120 shown in FIG. 4. The illumination area 160 represents the outermost edges of the field of illumination 132 through a full cycle of the moving reflector 156, such that the dashed line represents an edge when the reflector 156 is off-center to the left. In another embodiment, the wider illumination area 160 can be provided by swiveling or rotating the entire housing 150 or a lens within the housing instead of moving the reflector 156.

Figure 6:
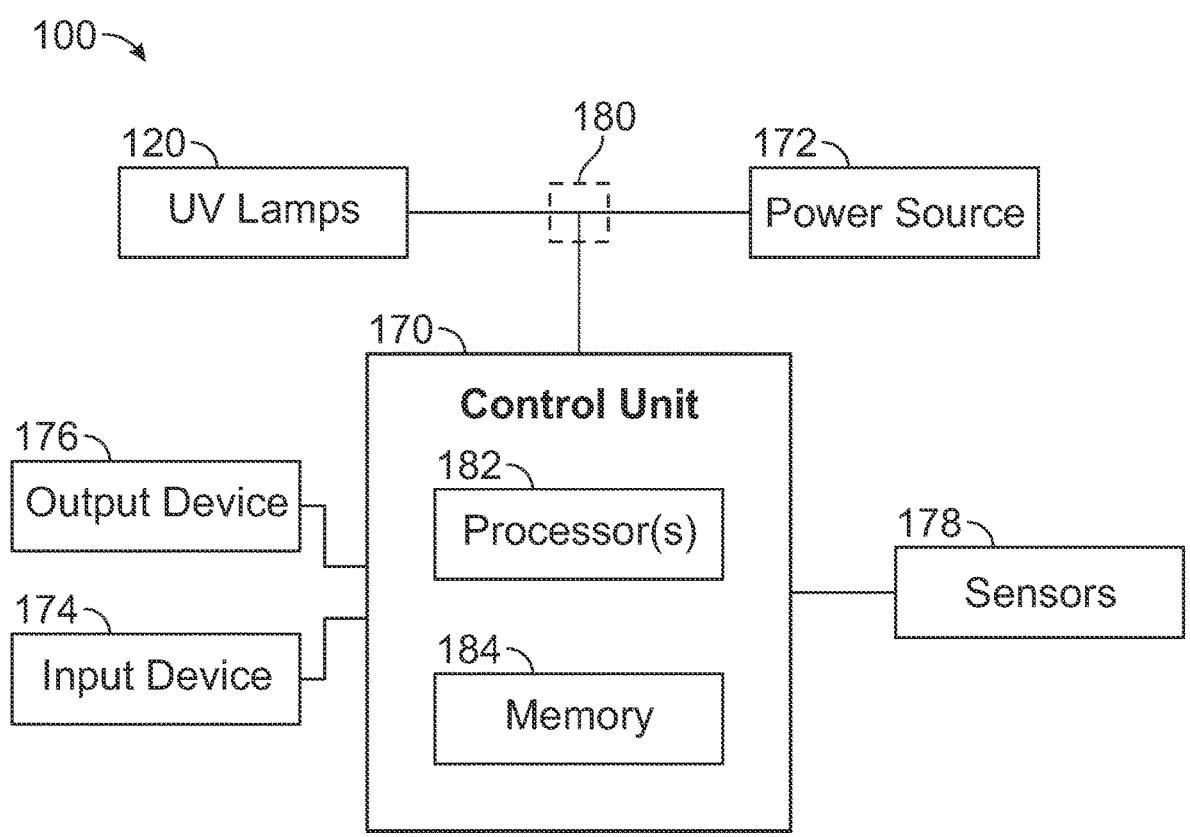
FIG. 6 is a schematic diagram of the sanitizing system according to an embodiment.

FIG. 6 is a schematic diagram of the sanitizing system 100 according to an embodiment. The sanitizing system 100 includes the UV lamps 120, a control unit 170, a power source 172, an input device 174, an output device 176, and sensors 178. The sensors 178 are optional such that one or more embodiments may lack sensors. The sanitizing system 100 is disposed onboard the aircraft. The UV lamps 120 represent the multitude of UV lamps 120 throughout the internal cabin 122 as shown in FIG. 2, including the UV lamps 120 in the PSUs 114 and along the ceiling 104. The power source 172 provides electrical power to the UV lamps 120 to power the generation of UV light. The power source 172 may be a generator that converts mechanical energy to electrical energy. Various electrically conductive wires and cables may conduct the electrical power from the power source 172 to the UV lamps 120. For example, the UV lamps 120 may utilize the same power source 172 and conductive pathways that supply power to other components in the cabin 122, such as the lights and blowers 115 in the PSUs 114. For example, the UV lamps 120 may plug into the same electronics package that controls cabin lighting.

The control unit 170 is operatively connected to the UV lamps 120, the input device 174, the output device 176, and the sensors 178 via wired and/or wireless communication pathways. The control unit 170 generates control signals that control the operations of the UV lamps 120. The control unit 170 represents hardware circuitry that includes and/or is connected with one or more processors 182 (e.g., one or more microprocessors, integrated circuits, microcontrollers, field programmable gate arrays, etc.). The control unit includes and/or is connected with a tangible and non-transitory computer-readable storage medium (e.g., memory) 184. For example, the memory 184 may store programmed instructions (e.g., software) that is executed by the one or more processors 182 to perform the operations of the control unit 170 described herein.

The control unit 170 can control the UV lamps 120 by controlling the presence and amount of electrical power (e.g., voltage and current) that is supplied to each of the UV lamps 120. Optionally, the control unit 170 is operatively connected to at least one switching device 180 along the circuit or bus between the power source 172 and the UV lamps 120. The switching device 180 is configured to selectively open (or break) a circuit to block power conduction to one or more of the UV lamps 120 and close (or establish) a circuit to enable power conduction to the one or more UV lamps 120. The switching device 180 may represent or include a solid-state relay, an electromechanical relay, an optical switch, a DC-DC converter, and/or the like. Although one switching device 180 is illustrated, the sanitizing system 100 may include multiple switching devices 180 that are independently controlled by the control unit 170. For example, each UV lamp 120 may have a different switching device 180 to enable independent control over each UV lamp 120. One or more of the switching devices 180 may enable variable control over the amount of power supplied to the associated UV lamps 120, besides merely turning the lamps 120 ON and OFF. For example, at least one switching device 180 can be controlled to supply full power to the associated UV lamps 120 and one or more reduced power levels, such as a medium power level and a low power level.

The input device 174 can represent or include a selector knob, a workstation computer, a tablet computer, a handheld computer (e.g., a smartphone), a keyboard, a touchpad, a joystick, and the like for enabling a pilot or another operator to control the sanitizing system 100. For example, an operator can enter a user input via the input device 174 for turning the UV lamps 120 ON and OFF, for selecting a power setting for one or more of the UV lamps 120, and/or for selecting an activity setting that controls one or more of the UV lamps 120. The output device 176 can be an integrated display device onboard the aircraft and/or a display screen on a personal computer, tablet, or handheld computer (e.g., smartphone). The control unit 170 may generate control signals for controlling the output device 176 to display a notification indicating the operating status of the sanitizing system 100. The operating status can include whether the sanitizing system 100 is ON or OFF and the power setting or level of the UV lamps 120. The operating status show the status of different subgroups that may be operating at different power settings. For example, the operating status may show that a UV lamp 120 in the lavatory is OFF while the UV lamps 120 in the PSUs 114 (shown in FIG. 2) are ON at a medium power setting.

In an embodiment, the sanitizing system 100 may be configured to automatically switch between different activity settings based on information received from the sensors 178 and/or other onboard systems. The activity settings can include boarding and deboarding, travel day, travel night, and OFF. For example, when the internal cabin 122 is empty (e.g., void of occupants), the sanitizing system 100 may operate in the OFF setting at which the UV lamps 120 are turned off and no UV light is emitted. The OFF setting is energy efficient because the sanitizing system 100 does not draw power to generate UV light. The control unit 170 may determine that the cabin 122 is empty based on one or more factors, such as the aircraft environmental control system being in the OFF state, the engines 14 and/or auxiliary power unit being in the OFF state, and the door to the aircraft being closed and locked. Optionally, the sensors 178 may include proximity sensors, motion sensors, and/or pressure sensors within the cabin 122. The sensors 178 may operate based on optical beams, passive infrared energy, microwave pulses, electrical induction, or the like. The control unit 170 may also determine that the cabin 122 is empty based on the proximity sensors, motion sensors, and/or pressure sensors indicating a lack of moving persons within the cabin 122.

During boarding prior to a trip (e.g., flight) and deboarding at the end of a trip, the control unit 170 operates the sanitizing system 100 in the boarding and deboarding setting. In this activity setting, the UV lamps 120 are operated in a high power level. The UV lamps generate and emit UV light at a high power output (relative to other activity settings) such that the emitted UV light has a high intensity. The UV lamps provide a stronger dose (e.g., amount of UV radiation per unit time) in the high power level relative to other power levels. The stronger dose is provided because the passengers and crew members are highly active during boarding and deboarding, as the passengers enter (or leave) the cabin 122, walk through the aisle 113, stow (or retrieve) their luggage, find (or exit) seats 110, and talk to other passengers. Because the spread of pathogens is increased during high activity events, the UV lamps 120 are operated in the high or full power levels to kill as many pathogens as possible. The control unit 170 can automatically determine that the boarding and deboarding is occurring based on the door to the aircraft being open (as indicated by a sensor that monitors door position), the aircraft being stationary, the environmental control system operating, and the like. Furthermore, the proximity, motion, and/or pressure sensors 178 can be used to detect an amount of movement in the cabin 122 during boarding and deboarding events. The control unit 170 may automatically switch the sanitizing system 100 to the boarding and deboarding setting based on one or more of the factors above. For example, the control unit 170 may switch to the boarding and deboarding setting responsive to data or signals from the sensors 178 that indicate that a level or amount of movement in the cabin 122 exceeds a designated threshold activity level. Optionally, an operator may utilize the input device 174 to manually instruct the control unit 170 which setting to implement, such as to instruct the control unit 170 to switch to the boarding and deboarding setting. Such manual control inputs may override the automated setting selection by the control unit 170.

During travel of the vehicle during the day, such as when the aircraft is at flight cruise, the control unit 170 may operate the sanitizing system 100 in the travel day setting. The travel day setting may represent a medium power level that is supplied to the UV lamps 120. During daytime travel, most of the passengers are seated, but some passengers may hold conversations with each other and others may exit their seats to stand, retrieve items from overhead stowage, use the lavatories, and the like. The activity level during daytime travel is less than the activity level during boarding and deboarding. The UV lamps 120 are operated with the medium power level, instead of the high power level, to continue sanitizing the air with UV light while at the same time conserving some electrical energy relative to operating in the high power level. It is noted that the UV lamps 120 may remain ON and continuously emitting UV light even when switching between different activity-based settings. The control unit 170 can automatically switch to the daytime travel setting based on factors that indicate that the aircraft is in flight and that it is daytime. The factors that indicate flight can include altimeter data, velocity data, engine settings, and the like. The factors that indicate daytime can include a clock and/or an ambient light sensor. For example, if in flight and the time is after 7 AM and before 7 PM, the control unit 170 may switch to the daytime flight setting.

During travel of the vehicle at night, the activity of the passengers may be reduced relative to during the day, as many of the passengers may be sleeping, reading, and watching videos on personal devices. The passengers may hold fewer conversations with each other relative to during the day. Upon determining that the aircraft is in flight during night, the control unit 120 is configured to switch the sanitizing system 100 to a travel night setting. The travel night setting may represent a low power level. The UV lamps 120 remain ON and emitting UV light in the lower power level, but at a reduced intensity or concentration than in the medium and high power levels. The lower power level conserves more electrical energy than the medium and high power levels. The control unit 170 may switch to the travel night setting upon detecting that the aircraft is in flight and the time is after 7 PM and before 7 AM, for example. In non-limiting examples, the high or full power level may supply 100% of the rated power of the UV lamps 120 to the UV lamps 120, the medium power level may supply 50%, 60%, or 66% of the rated power to the UV lamps 120, and the low power level may supply 25%, 33%, or 40% of the rated power to the UV lamps 120. The one or more switching devices 180 may be utilized to appropriately step down the power delivered to the UV lamps 120.

Optionally, the sensors 178 may include individual sensors disposed in each row of seats and configured to detect the presence of passengers in the seats of that row. For example, referring to FIG. 2, there may be a pressure sensor installed in each seat 110 that detects when a passenger is present on the seat 110 by the weight of the passenger. Optionally, a proximity sensor may be installed in the PSU 114 that detects when a passenger is present on the seat 110 by the proximity of that person to the proximity sensor. The control unit 170 receives the sensor data from the sensors 178 and analyzes the data to determine if any seats 110 and/or entire rows 112 of seats 110 on either side of the aisle 113 are unoccupied. For a given unoccupied seat 110, the control unit 170 may automatically reduce the power level supplied to the UV lamp 120 that is associated with that seat 110 by either turning the UV lamp 120 OFF or reducing to the low or medium power level. For example, the control unit 170 may reduce the power level of UV lamps 120 associated with unoccupied seats 110 one level below the current setting of the UV lamps 120 associated with occupied seats 110. Thus, if the current setting is the travel day setting with the UV lamps 120 in the medium power level, the control unit 170 controls the UV lamps 120 associated with unoccupied seats 110 in the low power level.

A method for sanitizing and disinfecting air and surfaces within an internal cabin of a vehicle is provided. The method may be performed by the sanitizing system 100 described above with reference to FIGS. 1-6. Certain steps of the method may be performed by the control unit 170 shown in FIG. 6 based on programmed logic or instructions. The method optionally includes additional steps than described, fewer steps than described, and/or different steps than described. The method includes supplying electrical power from a power source 172 onboard a vehicle 10 to a plurality of ultraviolet (UV) lamps 120 mounted at various locations within an internal cabin 122 of the vehicle 10. The method also includes controlling the UV lamps 120 to emit UV light into the internal cabin 122 on a continuous basis during a trip of the vehicle 10. The UV lamps 120 are positioned such that the emitted UV light disinfects air within the internal cabin 122 before passengers in the internal cabin 122 breathe the air.

Optionally, controlling the UV lamps 120 to emit the UV light includes controlling the UV lamps 120 to emit the UV light at a designated wavelength or narrow wavelength range that is safe for human tissue at prolonged exposure. Supplying the electrical power to the UV lamps 120 may include supplying the electrical power at a first power level during boarding and deboarding of the passengers in the internal cabin 122 and supplying the electrical power at a second power level that is less than the first power level during travel (e.g., movement) of the vehicle 10, such as flight of an aircraft.

As described herein, embodiments of the present disclosure provide systems and a methods for sanitizing and disinfecting surfaces, air, and people within an internal cabin of a vehicle on a continuous basis via UV light without harming the people exposed to the UV light. Further, embodiments of the present disclosure provide built-in, easy-to-use, and safe systems and methods for using UV light to sanitize air and surfaces within an internal vehicle cabin.

The sanitizing system 100 described with reference to FIGS. 1-6 disinfects pathogens in air and surfaces in aircraft cabin on a continuous basis. For example, 222 nm UV light may be on continuously (according to a duty cycle controlled by flight regime and crew). This allows disinfection for that flight regime at controlled or limited power. The UV light may kill pathogens both in the air and on surfaces near the lamp. The 222 nm UV may not be harmful to human tissue, while at the same time may be effective at killing pathogens. Thus, continuous exposure of an aircraft zone to 222 nm UV would both reduce pathogens in that zone and cause no harm to human occupants. In cabin seating areas of aircraft, 222 nm UV lighting can be deployed in a modulated way according to flight regime to maintain a constant or increased level of disinfection presence. This 222 nm lighting will continuously sanitize both the air and the surfaces of the cabin, including tray tables, seats, computer screens, individuals clothing, individuals skin, etc.

Further, the disclosure comprises embodiments according to the following clauses:

Clause 1. A sanitizing system comprising:
 a plurality of ultraviolet (UV) lamps mounted at various locations within an internal cabin of a vehicle, wherein the UV lamps are configured to receive electrical power from a power source onboard the vehicle and to emit UV light into the internal cabin on a continuous basis during a trip of the vehicle, wherein the UV lamps are positioned such that the emitted UV light disinfects air within the internal cabin.

Clause 2. The sanitizing system of Clause 1, wherein the various locations of the UV lamps are locations occupied by passengers and crew members during the trip.

Clause 3. The sanitizing system of Clause 1 or 2, wherein a subset of the UV lamps are mounted to a ceiling of the internal cabin and spaced apart along a length of the internal cabin, the subset configured to emit UV light from the ceiling all the way to a floor of an aisle.

Clause 4. The sanitizing system of any of Clauses 1-3, wherein a subset of the UV lamps are integrated into passenger service units (PSUs) disposed above each row of multiple rows of seats, the PSUs also including personal air blowers.

Clause 5. The sanitizing system of any of Clauses 1-4, wherein the UV lamps are configured to emit the UV light at a designated wavelength or narrow wavelength range that is safe for human tissue.

Clause 6. The sanitizing system of Clause 5, wherein the designated wavelength is 222 nm.

Clause 7. The sanitizing system of any of Clauses 1-6, wherein the UV lamps are controlled to persistently emit the UV light throughout an entire duration of the trip.

Clause 8. The sanitizing system of any of Clauses 1-7, further comprising a control unit including one or more processors and operatively connected to the UV lamps, the control unit configured to modify the electrical power supplied to one or more of the UV lamps during the trip based on activity of passengers such that the one or more UV lamps receive more electrical power when the passengers are more active than when the passengers are less active.

Clause 9. The sanitizing system of any of Clauses 1-8, further comprising a control unit and an input device, the control unit including one or more processors and operatively connected to the UV lamps and to the input device, wherein the control unit is configured to modify the electrical power supplied to one or more of the UV lamps based on a control signal received from the input device indicative of an operator manual selection.

Clause 10. The sanitizing system of any of Clauses 1-9, further comprising a control unit including one or more processors and operatively connected to the UV lamps, the control unit configured to operate one or more of the UV lamps at a first power level responsive to determining that passengers are boarding or deboarding the internal cabin.

Clause 11. The sanitizing system of Clause 10, wherein the control unit is configured to operate the one or more UV lamps at a second power level that is less than the first power level responsive to determining that the vehicle is traveling.

Clause 12. The sanitizing system of any of Clauses 1-11, further comprising a control unit including one or more processors and operatively connected to the UV lamps, the control unit configured to operate one or more of the UV lamps at a first power level responsive to determining that the vehicle is traveling during day time, and is configured to operate the one or more UV lamps at a second power level that is less than the first power level responsive to determining that the vehicle is traveling during night time.

Clause 13. The sanitizing system of any of Clauses 1-12, further comprising a control unit and a plurality of sensors associated with different seats in the internal cabin, the control unit including one or more processors and operatively connected to the UV lamps and to the sensors, wherein the control unit is configured to control one UV lamp of the UV lamps to cease emitting UV light responsive to determining, based on a signal received from one sensor of the sensors, that the seat associated with the one sensor is unoccupied.

Clause 14. The sanitizing system of any of Clauses 1-13, wherein the vehicle is an aircraft.

Clause 15. The sanitizing system of any of Clauses 1-14, wherein at least some of the UV lamps are positioned to emit the UV light in a field of illumination that extends between an air supply vent or a personal air blower and respective passengers in seats within the internal cabin such that the UV light disinfects air discharged from the air supply vent or the personal air blower before the passengers in the seats breathe the air.

Clause 16. A method comprising:
supplying electrical power from a power source onboard a vehicle to a plurality of ultraviolet (UV) lamps mounted at various locations within an internal cabin of the vehicle; and
controlling the UV lamps to emit UV light into the internal cabin on a continuous basis during a trip of the vehicle, the UV lamps positioned such that the emitted UV light disinfects air within the internal cabin before passengers in the internal cabin breathe the air.

Clause 17. The method of Clause 16, wherein controlling the UV lamps to emit the UV light includes controlling the UV lamps to emit the UV light at a designated wavelength or narrow wavelength range that is safe for human tissue at prolonged exposure.

Clause 18. The method of Clause 16 or 17, wherein supplying the electrical power to the UV lamps includes supplying the electrical power at a first power level during boarding and deboarding of the passengers in the internal cabin, and supplying the electrical power at a second power level that is less than the first power level during travel of the vehicle.

Clause 19. A sanitizing system comprising:
a plurality of ultraviolet (UV) lamps mounted at various locations within an internal cabin of a vehicle, the UV lamps configured to receive electrical power from a power source onboard the vehicle; and
a control unit including one or more processors and operatively connected to the UV lamps, the control unit configured to control the UV lamps to emit UV light into the internal cabin on a continuous basis during a trip of the vehicle, the control unit further configured to modify the electrical power supplied to one or more of the UV lamps during the trip based on activity of the passengers such that the one or more UV lamps receive more electrical power when the passengers are more active than when the passengers are less active.

Clause 20. The sanitizing system of Clause 19, wherein at least some of the UV lamps are positioned to emit the UV light in a field of illumination that extends between an air supply vent or a personal air blower and respective passengers in seats of the internal cabin such that the UV light disinfects air discharged from the air supply vent or the personal air blower before the passengers in the seats breathe the air.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

As used herein, value modifiers such as "about," "substantially," and "approximately" inserted before a numerical value indicate that the value can represent other values within a designated threshold range above and/or below the specified value, such as values within 5%, 10%, or 15% of the specified value.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing system comprising:
   ultraviolet (UV) lamps mounted at various locations within an internal cabin of a vehicle, wherein the UV lamps are configured to receive electrical power from a power source onboard the vehicle and to emit UV light into the internal cabin during a trip of the vehicle, wherein the UV lamps are positioned such that the emitted UV light disinfects air within the internal cabin; and
   a control unit including one or more processors and operatively connected to the UV lamps, the control unit configured to:
      operate one or more of the UV lamps at a first power level responsive to determining that passengers are boarding or deboarding the internal cabin, and
      operate the one or more UV lamps at a second power level that is less than the first power level responsive to determining that the vehicle is traveling.

2. The sanitizing system of claim 1, wherein a subset of the UV lamps are mounted to a ceiling of the internal cabin and spaced apart along a length of the internal cabin, the subset configured to emit UV light from the ceiling all the way to a floor of an aisle.

3. The sanitizing system of claim 1, wherein a subset of the UV lamps are integrated into passenger service units (PSUs) disposed above each row of multiple rows of seats, the PSUs also including personal air blowers.

4. The sanitizing system of claim 1, wherein the UV lamps are configured to emit the UV light at a designated wavelength or narrow wavelength range that is safe for human tissue.

5. The sanitizing system of claim 4, wherein the designated wavelength is 222 nm.

6. The sanitizing system of claim 1, wherein the UV lamps are controlled to persistently emit the UV light throughout an entire duration of the trip.

7. The sanitizing system of claim 1, the control unit further configured to modify the electrical power supplied to one or more of the UV lamps during the trip based on activity of passengers such that the one or more UV lamps receive more electrical power when the passengers are more active than when the passengers are less active.

8. The sanitizing system of claim 1, further comprising an input device, the control unit operatively connected to the input device, wherein the control unit is further configured to modify the electrical power supplied to one or more of the UV lamps based on a control signal received from the input device indicative of an operator manual selection.

9. The sanitizing system of claim 1, the control unit further configured to operate one or more of the UV lamps at a third power level responsive to determining that the vehicle is traveling during day time, and a fourth power level that is less than the third power level responsive to determining that the vehicle is traveling during night time.

10. The sanitizing system of claim 1, further comprising sensors associated with different seats in the internal cabin, the control unit operatively connected to the sensors, wherein the control unit is configured to control one UV lamp of the UV lamps to cease emitting UV light responsive to determining, based on a signal received from one sensor of the sensors, that the seat associated with the one sensor is unoccupied.

11. The sanitizing system of claim 1, wherein the vehicle is an aircraft.

12. The sanitizing system of claim 1, wherein at least some of the UV lamps are positioned to emit the UV light in a field of illumination that extends between an air supply vent or a personal air blower and respective passengers in seats within the internal cabin such that the UV light disinfects air discharged from the air supply vent or the personal air blower before the passengers in the seats breathe the air.

13. The sanitizing system of claim 1, wherein the various locations of the UV lamps are occupied by passengers and crew members during a trip of the vehicle.

14. A method comprising:
   supplying electrical power from a power source onboard a vehicle to ultraviolet (UV) lamps mounted at various locations within an internal cabin of the vehicle, wherein supplying the electrical power to the UV lamps includes supplying the electrical power at a first power level during boarding and deboarding of the passengers in the internal cabin, and supplying the electrical power at a second power level that is less than the first power level during travel of the vehicle; and
   controlling the UV lamps to emit UV light into the internal cabin during a trip of the vehicle, the UV lamps positioned such that the emitted UV light disinfects air within the internal cabin before passengers in the internal cabin breathe the air.

15. The method of claim 14, wherein controlling the UV lamps to emit the UV light includes controlling the UV lamps to emit the UV light at a designated wavelength or narrow wavelength range that is safe for human tissue at prolonged exposure.

16. The method of claim 14, wherein the various locations of the UV lamps are occupied by passengers and crew members during a trip of the vehicle.

17. A sanitizing system comprising:
   ultraviolet (UV) lamps mounted at various locations within an internal cabin of a vehicle, the UV lamps configured to receive electrical power from a power source onboard the vehicle; and
   a control unit including one or more processors and operatively connected to the UV lamps, the control unit configured to:
      control the UV lamps to emit UV light into the internal cabin during a trip of the vehicle,
      operate the one or more of the UV lamps at a first power level responsive to determining that the vehicle is traveling during day time, operate the one or more UV lamps at a second power level that is less than the first power level responsive to determining that the vehicle is traveling during night time, and modify the electrical power supplied to one or more of the UV lamps during the trip based on activity of the passengers such that the one or more UV lamps receive more electrical power when the passengers are more active than when the passengers are less active.

18. The sanitizing system of claim 17, wherein at least some of the UV lamps are positioned to emit the UV light in a field of illumination that extends between an air supply vent or a personal air blower and respective passengers in seats of the internal cabin such that the UV light disinfects air discharged from the air supply vent or the personal air blower before the passengers in the seats breathe the air.

19. The sanitizing system of claim 17, wherein the various locations of the UV lamps are occupied by passengers and crew members during a trip of the vehicle.

20. A sanitizing system comprising:
ultraviolet (UV) lamps mounted at various locations within an internal cabin of a vehicle, wherein the UV lamps are configured to receive electrical power from a power source onboard the vehicle and to emit UV light into the internal cabin during a trip of the vehicle, wherein the UV lamps are positioned such that the emitted UV light disinfects air within the internal cabin; and a control unit including one or more processors and operatively connected to the UV lamps, the control unit configured to:

operate one or more of the UV lamps at a first power level responsive to determining that the vehicle is traveling during day time, operate the one or more UV lamps at a second power level that is less than the first power level responsive to determining that the vehicle is traveling during night time.

21. A sanitizing system comprising:
ultraviolet (UV) lamps mounted at various locations within an internal cabin of a vehicle, wherein the UV lamps are configured to receive electrical power from a power source onboard the vehicle and to emit UV light into the internal cabin during a trip of the vehicle, wherein the UV lamps are positioned such that the emitted UV light disinfects air within the internal cabin; and a control unit and sensors associated with different seats in the internal cabin, the control unit including one or more processors and operatively connected to the UV lamps and to the sensors, wherein the control unit is configured to control one UV lamp of the UV lamps to cease emitting UV light responsive to determining, based on a signal received from one sensor of the sensors, that the seat associated with the one sensor is unoccupied.

\* \* \* \* \*